(12) United States Patent
Davis et al.

(10) Patent No.: US 8,313,506 B2
(45) Date of Patent: Nov. 20, 2012

(54) REATTACHABLE INTRODUCER FOR A MEDICAL DEVICE DEPLOYMENT SYSTEM

(75) Inventors: Champ Davis, Hollywood, FL (US); Stephen R. Healy, Miami, FL (US)

(73) Assignee: Codman & Shutleff, Inc., Raynham, MA (US)

( * ) Notice: Subject to any disclaimer, the term of this patent is extended or adjusted under 35 U.S.C. 154(b) by 0 days.

(21) Appl. No.: 13/192,733

(22) Filed: Jul. 28, 2011

(65) Prior Publication Data

US 2011/0282380 A1    Nov. 17, 2011

Related U.S. Application Data

(62) Division of application No. 11/363,898, filed on Feb. 28, 2006, now Pat. No. 8,133,252, which is a division of application No. 10/251,300, filed on Sep. 20, 2002, now Pat. No. 7,208,003.

(51) Int. Cl.
*A61M 29/00* (2006.01)

(52) U.S. Cl. .................................. 606/200; 604/104

(58) Field of Classification Search .................. 606/108, 606/191, 200; 623/1.11, 23.72; 604/96.01, 604/104

See application file for complete search history.

(56) References Cited

U.S. PATENT DOCUMENTS

| | | | |
|---|---|---|---|
| 3,550,591 A | 12/1970 | Macgregor |
| 3,853,130 A | 12/1974 | Sheridan |
| 4,175,564 A | 11/1979 | Kwak |
| 4,569,347 A | 2/1986 | Frisbie |
| 4,748,982 A | 6/1988 | Horzewski |
| 4,771,777 A | 9/1988 | Horzewski |
| 4,988,356 A | 1/1991 | Crittenden |
| 5,108,407 A | 4/1992 | Geremia |
| 5,122,136 A | 6/1992 | Guglielmi |
| 5,222,970 A | 6/1993 | Reeves |
| 5,263,964 A | 11/1993 | Purdy |
| 5,312,415 A | 5/1994 | Palermo |
| 5,324,269 A | 6/1994 | Miraki |
| 5,334,187 A | 8/1994 | Fischell |
| 5,334,210 A | 8/1994 | Gianturco |
| 5,350,397 A | 9/1994 | Palermo |
| 5,382,259 A | 1/1995 | Phelps |
| 5,458,605 A | 10/1995 | Klemm |
| 5,853,418 A | 12/1998 | Ken |
| 5,876,374 A | 3/1999 | Alba |
| 6,068,644 A | 5/2000 | Lulo |
| 6,113,622 A | 9/2000 | Hieshima |
| 6,117,142 A | 9/2000 | Goodson |
| 6,174,327 B1 | 1/2001 | Mertens |
| 6,179,857 B1 | 1/2001 | Diaz |
| 6,183,491 B1 | 2/2001 | Lulo |
| 6,196,995 B1 | 3/2001 | Fagan |
| 6,206,844 B1 | 3/2001 | Reichel |

(Continued)

FOREIGN PATENT DOCUMENTS

FR    2757406 A1    6/1998

(Continued)

*Primary Examiner* — Victor Nguyen

(57) ABSTRACT

A reattachable introducer and method of using such introducer is disclosed for inserting an embolic coil deployment system into the tortuous vasculature of the human brain for placing an embolic coil within an aneurysm. The introducer includes a sheath having a lumen, a side opening and a longitudinal slit and includes a cylindrical sleeve slideably disposed about the sheath. A deployment catheter with a conical expander member is slideably disposed through the side opening of the sheath and through the lumen of the sheath. The conical expander member detaches the introducer from the deployment catheter through the longitudinal slit of the sheath, while the cylindrical sleeve reattaches the introducer to the deployment catheter through the longitudinal slit.

8 Claims, 2 Drawing Sheets

U.S. PATENT DOCUMENTS

| | | |
|---|---|---|
| 6,254,612 B1 | 7/2001 | Hieshima |
| 6,277,125 B1 | 8/2001 | Barry |
| 6,280,414 B1 | 8/2001 | Shah |
| 6,338,730 B1 * | 1/2002 | Bonutti et al. .............. 604/509 |
| 6,379,374 B1 | 4/2002 | Hieshima |
| 7,018,394 B2 | 3/2006 | Diaz |

FOREIGN PATENT DOCUMENTS

| | | |
|---|---|---|
| JP | 50086884 A | 7/1975 |
| WO | WO 02054943 A2 | 7/2002 |

* cited by examiner

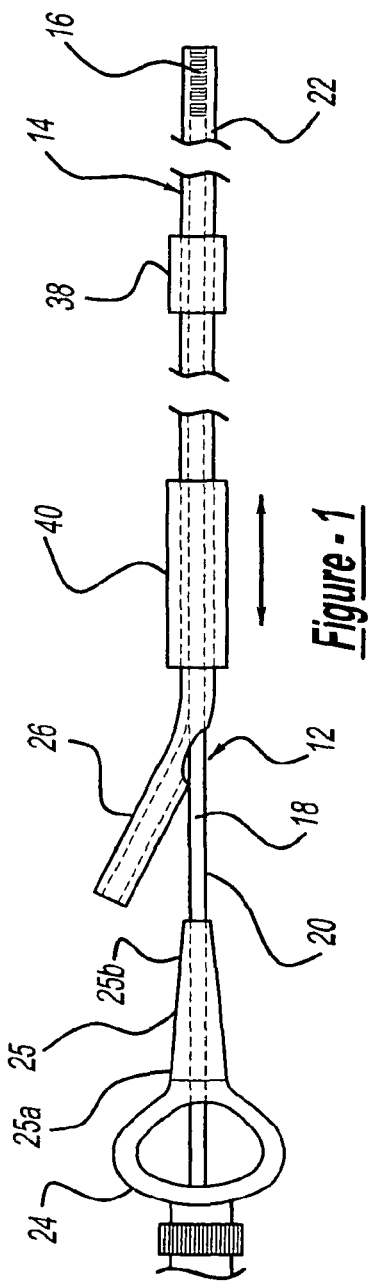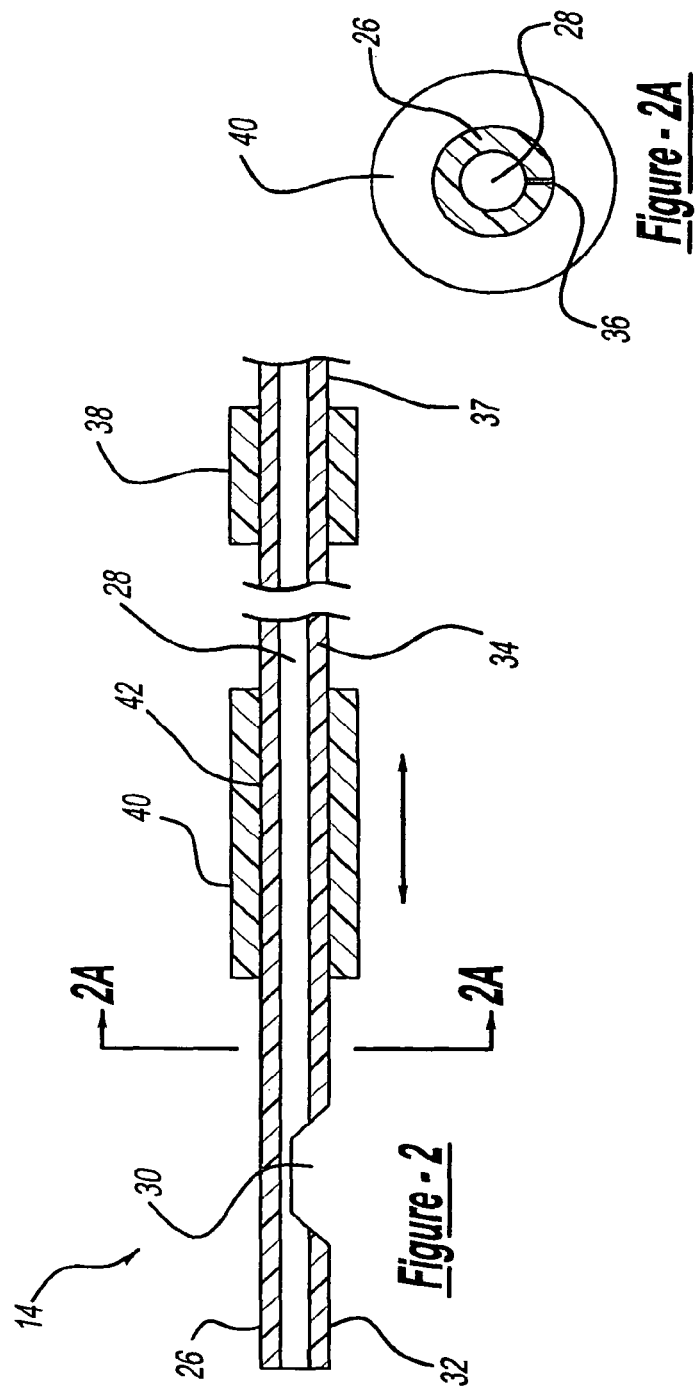

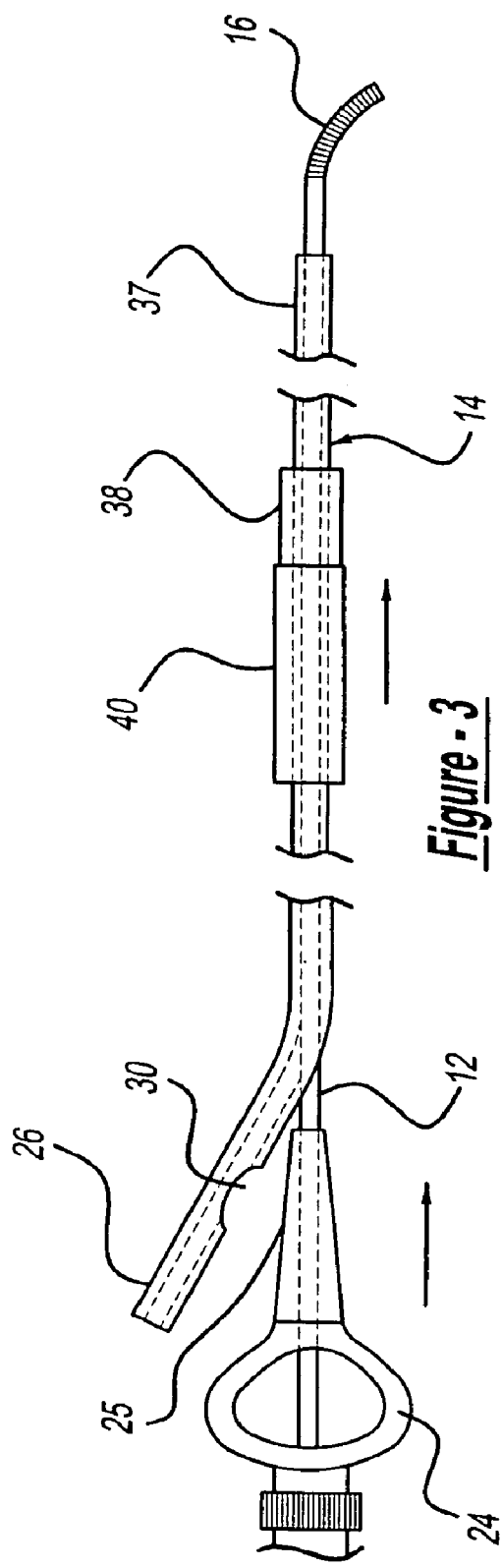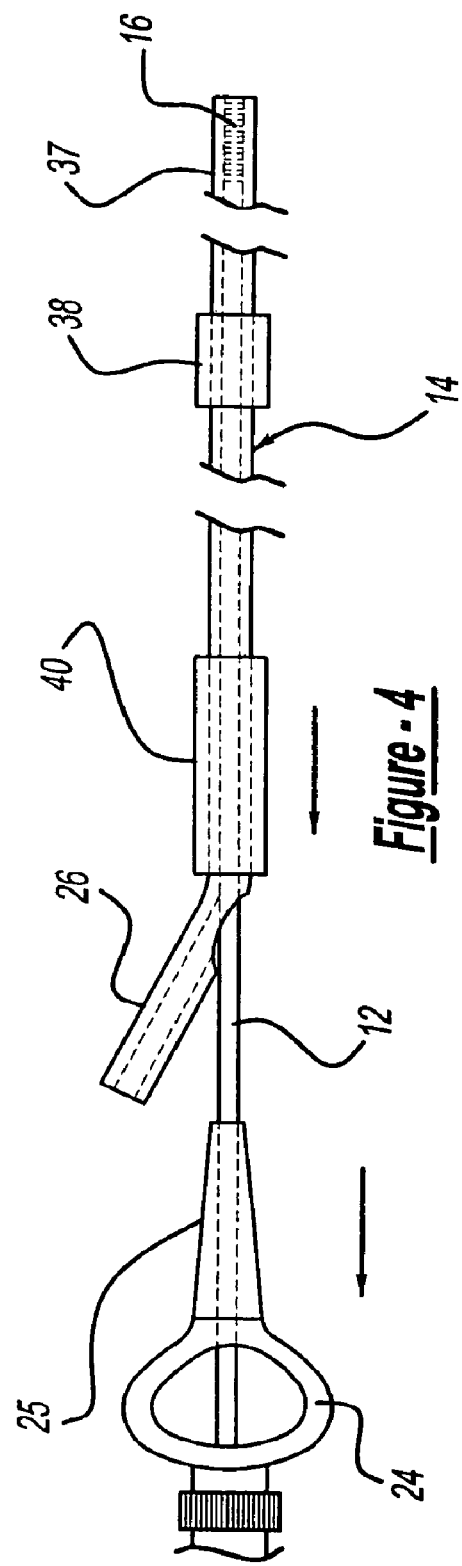

REATTACHABLE INTRODUCER FOR A MEDICAL DEVICE DEPLOYMENT SYSTEM

CROSS REFERENCE TO RELATED APPLICATION

The present application is a divisional patent application of U.S. patent application Ser. No. 11/363,898, filed Feb. 28, 2006, which is a divisional of U.S. patent application Ser. No. 10/251,300, filed Sep. 20, 2002, (now U.S. Pat. No. 7,208,003, issued Apr. 24, 2007).

BACKGROUND OF THE INVENTION

1. Field of the Invention

This invention relates to a reattachable introducer for inserting a medical device deployment system into the vasculature of a human body and further relates to a method of using such introducer. The deployment system may be used for placing a medical device at a preselected position within a vessel. More particularly, the introducer is suited for inserting an embolic coil deployment system into the tortuous vasculature of the human brain for placing an embolic coil within an aneurysm.

2. Description of the Prior Art

For many years physicians have been placing various devices within a blood vessel of the human body in order to treat an aneurysm or to occlude a vessel. These devices are placed within the aneurysm or vessel using one of several different catheter deployment systems. These deployment systems transport and release the devices at a particular location within the vessel. The combination of different devices and different deployment systems provide physicians with reliable methods of treating aneurysms.

Physicians place various types of devices within an aneurysm or a vessel to occlude the flow of blood by promoting thrombus formation. Such devices include dilatation balloons, liquid medications, and embolic coils. Embolic coils may take the form of helically wound coils, randomly wound coils, coils wound within other coils, and many other coil configurations. These coils are generally formed of radiopaque metallic materials, such as platinum, gold, and tungsten, or alloys of these metals. Often times, several coils are placed at a given location in order to occlude the flow of blood through the vessel.

U.S. Pat. No. 6,179,857, entitled, "Stretch Resistant Embolic Coil With Variable Stiffness" discloses one example of such an embolic coil design. The coil disclosed in this patent is a helically wound coil, and various combinations of adjacent turns are spot welded together to create a stretch resistant coil of varying flexibility. U.S. Pat. No. 6,183,491, entitled, "Embolic Coil Deployment System With Improved Embolic Coil" discloses another embolic coil configuration which has a relatively flexible proximal portion which resists stretching.

Also, U.S. Pat. No. 5,853,418, entitled "Stretch Resistant Vaso-occlusive Coils," discloses a helically wound coil having a polymeric stretch resistant member extending through the lumen of the coil and fixedly attached to both the distal end and the proximal end of the coil. Other examples of coil configurations are disclosed in U.S. Pat. No. 5,334,210, entitled, "Vascular Occlusion Assembly" and U.S. Pat. No. 5,382,259 entitled, "Vasoocclusion Coil With Attached Tubular Woven Or Braided Fibrous Covering." With all such coil designs, it is important that the coils remain very flexible so that they may be passed through vessels with the use of a catheter deployment system.

A variety of coil deployment systems are available for placing embolic coils within an aneurysm or vessel. U.S. Pat. No. 6,113,622, entitled, "Embolic Coil Hydraulic Deployment System" and assigned to the same assignee as the present patent application discloses one example of such a deployment system. The hydraulic embolic coil deployment system disclosed in this patent uses fluid pressure which is applied to the lumen of the deployment catheter for expanding the distal section radially thereby releasing the embolic coil at a preselected position.

U.S. Pat. No. 5,350,397, entitled, "Axially Detachable Embolic Coil Assembly" discloses another known coil deployment system which utilizes a deployment catheter having a socket at the distal end for retaining a ball which is bonded to the proximal end of the embolic coil. The ball is placed within the socket at the distal end of the deployment catheter, and the deployment system is then moved into a vessel to place the coil at a desired position. A pusher wire with a piston at its distal end is pushed distally from the proximal end of the deployment catheter to thereby push the ball out of the socket and release the coil at the desired position.

Also, U.S. Pat. No. 5,263,964, entitled, "Coaxial Traction Detachment Apparatus and Method" discloses still another coil deployment system. The system disclosed in this patent uses glue or solder for attaching an embolic coil to a guidewire which is, in turn, pushed through a flexible catheter for positioning the coil within the vessel at a preselected position. Once the coil is at the desired position, the coil is restrained by the deployment catheter, and the guidewire is pulled from the proximal end of the coil causing the coil to become detached from the guidewire and released from the deployment system.

Additionally, U.S. patent application Ser. No. 09/580,684 entitled, "Small Diameter Embolic Coil Hydraulic Deployment System," filed on May 30, 2000 and assigned to the same assignee as the present patent application, discloses a vasoocclusive coil deployment system for placing a small diameter coil. In the system disclosed in this patent, the distal end of a cylindrical headpiece is inserted into and bonded to the embolic coil. The proximal end of the cylindrical headpiece has a diameter approximately equal to the diameter of the lumen of a deployment catheter so that the cylindrical headpiece is disposed in fluid-tight engagement with the lumen of the deployment catheter. When fluid pressure is applied to the lumen of the deployment catheter, the outer wall of the distal section of the deployment catheter expands radially and releases the cylindrical headpiece along with the embolic coil.

Examples of other such coil deployment systems are disclosed in U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas" and U.S. Pat. No. 5,108,407, entitled, "Method And Apparatus For Placement Of An Embolic Coil."

SUMMARY OF THE INVENTION

In accordance with one aspect of the present invention, there is provided an embolic coil deployment system and reattachable introducer therefor which includes a sheath which takes the form of an elongated flexible tubular member having a lumen extending therethrough and having a proximal end, a distal end and an outer wall. The sheath has a side opening in the outer wall of the sheath adjacent to the proximal end of the sheath. The sheath also has a longitudinal slit extending through the outer wall of the sheath and extending from the side opening and in a direction toward the distal end of the sheath. The reattachable introducer also includes a cylindrical sleeve which is slideably disposed about the sheath and is movable between the side opening of the sheath and the distal end of the sheath. Furthermore, the embolic coil deployment system includes a deployment catheter having a lumen extending therethrough and having a proximal section and a distal section. The deployment catheter is slideably disposed through the side opening of the sheath and through the lumen of the sheath. Finally, the embolic coil deployment system includes a vascular occlusive embolic coil being detachably attached to the distal section of the deployment catheter.

In accordance with another aspect of the present invention, there is provided a reattachable introducer for use with an embolic coil deployment catheter to place an embolic coil into an aneurysm. The introducer includes a sheath which takes the form of an elongated flexible tubular member having a lumen extending therethrough and having a proximal end, a distal end and an outer wall. The sheath has a side opening in the outer wall of the sheath adjacent to the proximal end of the sheath. The sheath also has a longitudinal slit extending through the outer wall of the sheath and extending from said side opening toward the distal end of the sheath. The introducer further includes a cylindrical sleeve which is slideably disposed about the sheath and is movable between the side opening of the sheath and the distal end of the sheath.

In accordance with still another aspect of the present invention, there is provided a medical device deployment system and reattachable introducer therefor which includes a sheath which takes the form of an elongated flexible tubular member having a lumen extending therethrough and having a proximal end, a distal end and an outer wall. The sheath has a side opening in the outer wall of the sheath adjacent to proximal end of the sheath. The sheath also has a longitudinal slit extending through the outer wall of the sheath and extending from the side opening and in a direction toward the distal end of the sheath. The reattachable introducer also includes a cylindrical sleeve which is slideably disposed about the sheath and is movable between the side opening of the sheath and the distal end of the sheath. Furthermore, the medical device deployment system includes a deployment catheter having a lumen extending therethrough and having a proximal section and a distal section. The deployment catheter is slideably disposed through the side opening of the sheath and through the lumen of the sheath. Finally, the medical device deployment system includes a medical device being attached to the distal section of the deployment catheter.

In accordance with another aspect of the present invention, the deployment catheter includes a conical expander member having a base portion. The conical expander member tapers from the base portion to form a tip portion. The conical expander member is coaxially disposed about the deployment catheter with the tip portion of the conical expander member extending distally from the base portion of the conical expander member so that as the deployment catheter is moved distally the expander member causes the longitudinal slit to open thereby causing the sheath to separate from the deployment catheter.

In accordance with another aspect of the present invention, the sheath includes a sheath stop which takes the form of a projection disposed on the outer wall of the sheath at a position proximal to the distal end of the sheath.

In accordance with still another aspect of the present invention, the sheath includes a sheath stop which takes the form of a cylindrical ring having a lumen extending therethrough. The sheath stop is fixedly disposed about the outer wall of the sheath at a position proximal to the distal end of the sheath.

In accordance with yet another aspect of the present invention, the longitudinal slit of the sheath extends from the side opening to the sheath stop, and the deployment catheter includes a winged hub attached to the proximal section of the deployment catheter.

In accordance with another aspect of the present invention, the side opening is generally circular and the side opening has a diameter greater than an outside diameter of the deployment catheter.

In accordance with still another aspect of the present invention, the side opening is generally oval in shape. The side opening has a major axis and a minor axis. The major axis of the side opening is generally parallel with a longitudinal axis of the sheath. The minor axis of the side opening is generally greater than an outside diameter of the deployment catheter.

In accordance with another aspect of the present invention, there is provided a method for placing an embolic coil within an aneurysm or for placing a medical device at a preselected position within a vessel. The method includes the step of providing a delivery catheter; a reattachable introducer including a sheath having a lumen, a side opening and a longitudinal slit; a cylindrical sleeve disposed about the sheath; a deployment catheter being slideably disposed through the side opening of the sheath and through the lumen of the sheath; and a vascular occlusive embolic coil or medical device being attached to the distal section of the deployment catheter. The method also includes the step of inserting the delivery catheter into the vasculature of the body then inserting the deployment catheter and introducer into a lumen of the delivery catheter.

Moreover, the method includes the step of sliding the cylindrical sleeve distally from the side opening of the sheath and toward the distal end of the sheath. The method also includes the step of pushing the deployment catheter distally through the side opening causing the sheath to detach from the deployment catheter through the longitudinal slit thereby causing the embolic coil or medical device to become exposed. The method further includes the step of releasing the embolic coil within the aneurysm or the medical device at the preselected position then removing the deployment catheter and introducer. Finally, the method includes the step of removing the delivery catheter from the body.

In accordance with still another aspect of the present invention, there is provided a method for retrieving a deployment catheter and an embolic coil or medical device from the body. The method includes the step of providing a delivery catheter; a reattachable introducer including a sheath having a lumen, a side opening and a longitudinal slit; a cylindrical sleeve disposed about the sheath; a deployment catheter being slideably disposed through the side opening of the sheath and through the lumen of the sheath; and a vascular occlusive embolic coil or medical device being attached to the distal section of the deployment catheter. The method also includes the step of inserting the delivery catheter into the vasculature of the body then inserting the deployment catheter and introducer into a lumen of the delivery catheter.

Moreover, the method includes the step of sliding the cylindrical sleeve distally from the side opening of the sheath and toward the distal end of the sheath. The method also includes the step of pushing the deployment catheter distally through the side opening causing the sheath to detach from the deployment catheter through the longitudinal slit thereby causing the embolic coil or medical device to become exposed. The method further includes the step of pulling the deployment catheter proximally thereby causing the embolic coil or medical device to become disposed within the lumen of the sheath then sliding the cylindrical sleeve proximally toward the side opening of the sheath thereby causing the sheath to reattach about the deployment catheter through the longitudinal slit and causing the sheath to pinch the deployment catheter thereby preventing the sheath from sliding along the deployment catheter. Finally, the method includes the step of removing the deployment catheter, introducer and delivery catheter from the body.

BRIEF DESCRIPTION OF THE DRAWINGS

FIG. 1 is an enlarged perspective view of an embolic coil deployment system with an introducer disposed about a deployment catheter;

FIG. 2 is an enlarged, sectional view of the introducer in accordance with the present invention;

FIG. 2a is an enlarged, cross-sectional view of the introducer of FIG. 2 showing a longitudinal slit in an outer wall of the sheath;

FIG. 3 is an enlarged perspective view of the embolic coil deployment system and introducer showing the deployment catheter being moved distally, forcing the sheath off the deployment catheter and pushing an embolic coil out the end of the sheath; and, FIG. 4 is an enlarged perspective view of the embolic coil deployment system and introducer showing the deployment catheter and cylindrical sleeve being moved proximally thereby pulling the embolic coil back into the sheath and forcing the sheath back onto the deployment catheter.

DESCRIPTION OF THE PREFERRED EMBODIMENT

FIG. 1 illustrates a deployment catheter 12, a reattachable introducer 14, and an embolic coil 16. The deployment catheter 12 is an elongated tube with a lumen 18. Preferably, the proximal section 20 of the deployment catheter 12 is formed of a pellethane material having a durometer in a range of about 60 D to 75 D. The proximal section 20 is sufficiently flexible to transverse the vasculature of the human body, but is sufficiently rigid so that it can be pushed distally through the introducer 14. The distal section 22 of the deployment catheter 12 is preferably formed of a pellethane material having a durometer of between 25 D and 55 D with a durometer of 40 D being the preferred durometer.

The deployment catheter 12 also includes a winged hub 24 coupled to the proximal section 20 of the deployment catheter 12. The winged hub 24 may be made from plastic and aids in the insertion of the deployment catheter 12 into the vasculature of the body. Furthermore, the deployment catheter 12 includes a conical expander member 25. The conical expander member 25 is coaxially disposed about the deployment catheter 12 and tapers from its base portion 25a to its tip portion 25b. The tip portion 25b of the conical expander member 25 is distal the base portion 25a. The conical expander member 25 is preferably made from the same material as the winged hub 24. Finally, the deployment catheter 12 includes an embolic coil 16 attached to the distal section 22 of the deployment catheter 12. The embolic coil 16 may take various forms and configurations and may even take the form of a randomly wound coil, however, a helically wound flexible embolic coil is illustrated in FIG. 1.

FIG. 2 illustrates the introducer 14 which includes a sheath 26 which is approximately 80 centimeters in length and is formed of a polymer material with a durometer in the range of about 50 D and 80 D. The sheath 26 has a diameter of approximately 0.1 centimeters, and the lumen 28 of the sheath 26 has a diameter slightly greater than an outside diameter of the deployment catheter 12. The sheath 26 includes a side opening 30 adjacent to the proximal end 32 of the sheath 26. The side opening 30 is a hole cut in the outer wall 34 of the sheath 26 and extends through the outer wall 34 and into the lumen 28 of the sheath 26. The side opening 30 may take the form of a circle cut through the outer wall 34 of the sheath 26 or may take other configurations, like an oval. Preferably, the side opening 30 has a diameter in the range of about 0.23 centimeters to 0.38 centimeters. The sheath 26 also includes a longitudinal slit 36 in the outer wall 34 of the sheath 26. The longitudinal slit 36 is approximately 60 centimeters in length and extends from the side opening 30 and in a direction toward the distal end 37 of the sheath 26.

The introducer 14 also includes a sheath stop 38 which is disposed about the outer wall 34 of the sheath 26 at a position proximal to the distal end 37 of the sheath 26. The sheath stop 38 is cylindrical in shape and is made of nylon but may also be formed from plastic or a polymer. The length of the sheath stop 38 is approximately 1.3 centimeters while the preferred diameter of the sheath stop 38 is 0.18 centimeters. A cylindrical sleeve 40 is slideably disposed about the sheath 26 and is approximately 4.5 centimeters in length. The cylindrical sleeve 40 is generally cylindrical in shape and has a lumen 42. The cylindrical sleeve 40 is formed of polyethylene but may also be made from plastic or a polymer. The lumen 42 of the cylindrical sleeve 40 has a diameter slightly greater than the outside diameter of the sheath 26. Preferably, the outside diameter of the cylindrical sleeve 40 is 0.18 centimeters.

FIG. 2A illustrates a cross sectioned view of the sheath 26 between the side opening 30 and the cylindrical sleeve 40. The longitudinal slit 36 runs through the outer wall 34 of the sheath 26 and into the lumen 28 of the sheath 26. The cylindrical sleeve 40 is slideably disposed about the sheath 26.

FIG. 3 illustrates the winged hub 24, conical expander member 25 and deployment catheter 12 being moved distally through the side opening 30 of the sheath 26, forcing the sheath 26 to separate from the deployment catheter 12 through the longitudinal slit 36 and pushing the embolic coil 16 out the distal end 37 of the sheath 26.

FIG. 4 illustrates the winged hub 24, conical expander member 25 and deployment catheter 12 being moved proximally, pulling the embolic coil 16 back into the distal end 37 of the sheath 26. The cylindrical sleeve 40 is moved proximally over the sheath 26 causing the sheath 26 to reattach about the deployment catheter 12 through the longitudinal slit 36.

The introducer operates to place an embolic coil into an aneurysm of the brain. With the introducer slideably disposed over a deployment catheter, the cylindrical sleeve is positioned generally over the side opening causing the introducer to be pinched to the deployment catheter. In this configuration, the deployment catheter and introducer can be inserted into a delivery catheter. The sheath of the introducer protects an embolic coil as the distal section of the deployment catheter is inserted into the patient. The deployment catheter and introducer are inserted until the sheath stop generally reaches the proximal end of the delivery catheter. At this point, the cylindrical sleeve is moved distally to expose the side opening. Then, the deployment catheter is moved distally causing the conical expander member to move distally and forcing the sheath off the deployment catheter. The sheath allows the deployment catheter to enter the vasculature more easily; otherwise, the flexible deployment catheter would bend as it was being pushed distally. At the same time the sheath is separating from the deployment catheter, the embolic coil attached to the distal section of the deployment catheter exits the sheath.

From this position, the physician can deploy the embolic coil at a preselected position within a vessel. Once the coil is no longer attached to the deployment catheter, the deployment catheter and introducer are removed from the vasculature and another deployment catheter and introducer are introduced in the same manner when more coils are required.

If, before the embolic coil is deployed, the physician decides to retrieve the coil, the sheath can be reattached, and the system can be reused. To do this, the deployment catheter is pulled proximally until the embolic coil is again disposed within the sheath. Then, the cylindrical sleeve is slid proximally, reattaching the sheath onto the deployment catheter through the longitudinal slit. The cylindrical sleeve is then slid generally over the side opening to hold the sheath to the deployment catheter. Finally, the deployment catheter and introducer are removed from the patient.

A novel system has been disclosed in which an introducer is used to introduce an embolic coil deployment system into the vasculature of the body. Although a preferred embodiment of the invention has been described, it is to be understood that various modifications may be made by those skilled in the art without departing from the scope of the present invention. For example, there are many variations and modifications of the embolic coil, including numerous coil winding configurations, or alternatively, other types of vascular occlusive devices may be utilized, such as dilation balloons, radiopaque fluids, and liquid medications.

These and other modifications would be apparent to those having ordinary skill in the art to which this invention relates and are intended to be within the scope of the claims which follow.

That which is claimed is:

1. A reattachable introducer for use with an embolic coil deployment catheter to place an embolic coil into an aneurysm, said introducer comprising:
    a sheath which takes the form of an elongated, flexible tubular member having a lumen extending therethrough and having a proximal end, a distal end, and an outer wall, said sheath having a side opening in the outer wall of said sheath adjacent to the proximal end of said sheath, said sheath having a longitudinal slit extending through the outer wall of said sheath and extending from said side opening toward the distal end of said sheath; and
    a cylindrical sleeve slideably disposed about said sheath and being movable between said side opening of said sheath toward the distal end of said sheath, said cylindrical sleeve being short enough to move beyond said side opening and at least some of said slit when moved toward said distal end, without extending beyond said distal end, said cylindrical sleeve being also capable when moved to said side opening of causing the sheath to pinch a deployment catheter which is extending through said side opening and also extending proximally from said side opening through said sheath, thereby preventing the sheath from sliding along the deployment catheter; wherein said sheath includes a sheath stop which takes the form of a cylindrical ring having a lumen extending therethrough, said sheath stop being fixedly disposed about the outer wall of said sheath at a position proximal to the distal end of said sheath.

2. A reattachable introducer as defined in claim 1, wherein said longitudinal slit of said sheath extends from said side opening to said sheath stop.

3. The reattachable introducer of claim 1 in which said side opening is of greater diameter than the outer diameter of said deployment catheter.

4. A reattachable introducer for use with a medical device deployment catheter to place a medical device at a preselected position within a vessel, said reattachable introducer comprising:
    a sheath which takes the form of an elongated flexible tubular member having a lumen extending therethrough and having a proximal end, a distal end, and an outer wall, said sheath having a side opening in the outer wall of said sheath adjacent to the proximal end of said sheath, said sheath having a longitudinal slit extending through the outer wall of said sheath and extending from said side opening toward the distal end of said sheath;
    a cylindrical sleeve slideably disposed about said sheath and being movable between said side opening of said sheath and the distal end of said sheath, said cylindrical sleeve being short enough to move beyond said side opening and at least some of said slit when moved toward said distal end, without extending beyond said distal end; and
    said cylindrical sleeve being also capable when moved to said side opening of causing the sheath to pinch a deployment catheter which is extending through said side opening and also extending proximally from said side opening through said sheath, thereby preventing the sheath from sliding along the deployment catheter; wherein said side opening is of greater diameter than the outer diameter of said deployment catheter.

5. A reattachable introducer as defined in claim 4, wherein said sheath includes a sheath stop which takes the form of a projection disposed on the outer wall of said sheath at a position proximal to the distal end of said sheath.

6. A reattachable introducer as defined in claim 5, wherein said sheath includes a sheath stop which takes the form of a cylindrical ring having a lumen extending therethrough, said sheath stop being fixedly disposed about the outer wall of said sheath at a position proximal to the distal end of said sheath.

7. A reattachable introducer as defined in claim 6, wherein said longitudinal slit of said sheath extends from said side opening to said sheath stop.

8. A reattachable introducer as defined in claim 5, wherein said longitudinal slit of said sheath extends from said side opening to said sheath stop.

* * * * *